US008623190B2

(12) United States Patent
Brückner et al.

(10) Patent No.: US 8,623,190 B2
(45) Date of Patent: Jan. 7, 2014

(54) DEVICE AND METHOD FOR PERFORMING MAINTENANCE ON AN APPARATUS IN A FLOW DUCT

(75) Inventors: Uwe Brückner, Altdorf (DE); Ingo Riesen, Lauf an der Pegnitz (DE)

(73) Assignee: Siemens Aktiengesellschaft, München (DE)

(*) Notice: Subject to any disclaimer, the term of this patent is extended or adjusted under 35 U.S.C. 154(b) by 1149 days.

(21) Appl. No.: 12/085,542

(22) PCT Filed: Nov. 6, 2006

(86) PCT No.: PCT/EP2006/068111
§ 371 (c)(1),
(2), (4) Date: Jan. 22, 2009

(87) PCT Pub. No.: WO2007/060087
PCT Pub. Date: May 31, 2007

(65) Prior Publication Data
US 2009/0120807 A1    May 14, 2009

(30) Foreign Application Priority Data

Nov. 28, 2005 (EP) .................................... 05025907

(51) Int. Cl.
*G01N 27/26* (2006.01)
(52) U.S. Cl.
USPC ............ 204/433; 204/435; 204/432; 324/428

(58) Field of Classification Search
USPC .......... 324/438–450; 204/415–416, 433, 435; 73/1.01–1.08
See application file for complete search history.

(56) References Cited

U.S. PATENT DOCUMENTS 4,490,236 A * 12/1984 Petty .............................. 204/409
7,886,571 B2 * 2/2011 Lee et al. ........................ 73/1.01

FOREIGN PATENT DOCUMENTS

| DE | 1 802 030 | 4/1970 |
| DE | 33 15 509 A1 | 11/1983 |
| EP | 0 223 948 A2 | 6/1987 |
| EP | 0 281 184 A2 | 9/1988 |
| EP | 0 372 121 A1 | 6/1990 |

* cited by examiner

*Primary Examiner* — Keith Hendricks
*Assistant Examiner* — Bach Dinh

(57) ABSTRACT

The invention relates to a device and a method for performing maintenance on an apparatus. The device has a flow duct with a wall section in which at least one apparatus which projects into the flow duct and which is to be reworked after a certain operating time is arranged. A vessel which is open towards the wall section is arranged to as to be movable relative to the wall section in such a way that in an open position it is arranged at a distance from the apparatus, and in a second position forms, together with the wall section, a sealed volume which is separated from the rest of the flow duct and in which the maintenance of the apparatus is performed.

19 Claims, 2 Drawing Sheets

DEVICE AND METHOD FOR PERFORMING MAINTENANCE ON AN APPARATUS IN A FLOW DUCT

CROSS REFERENCE TO RELATED APPLICATIONS

This application is the US National Stage of International Application No. PCT/EP2006/068111, filed Nov. 6, 2006 and claims the benefit thereof. The International Application claims the benefits of European application No. 05025907.6 filed Nov. 28, 2005, both of the applications are incorporated by reference herein in their entirety.

FIELD OF INVENTION

Due to the accumulation of solid matter on the measuring device, measurement of a value in a suspension by means of a measuring apparatus results in the contamination thereof. For example, measurement of a pH value of a milk of lime suspension of a flue gas scrubber is particularly subject to contamination by the high solids content. The pH electrode must be separated from the process medium for rinsing and calibration.

BACKGROUND OF THE INVENTION

Conventional systems operate externally on a bypass basis, which is complex and expensive, or incorporated in the process, the electrode being mechanically withdrawn from the process in order to rinse and calibrate it. Because of the solids such as sand that are always contained in the milk of lime, the metal surfaces of the fittings are heavily stressed and often become clogged. Automatic maintenance by means of cleaning/calibration is then no longer possible.

SUMMARY OF INVENTION

The object of the present invention is therefore to specify a device which allows automatic maintenance of an apparatus.

This object is achieved by the device as claimed in the claims.

Another object of the present invention is to specify a method which allows automatic maintenance of an apparatus.

This object is achieved by the method as claimed in the claims.

The device according to the invention has a flow duct with a wall section and a container which moves relative to the wall section, said container being open toward said wall section. At least one apparatus can be mounted in a fixed manner in the wall section. The container is movably disposed such that, in a first position, it forms a closed three-dimensional space with the wall section, while, in a second position, it is at a distance from the wall section such that it forms no closed three-dimensional space with the wall section. By means of the device according to the invention, the wall section and the apparatus mounted thereon can be sealed against its environment.

In a preferred embodiment the at least one apparatus is an electrode, preferably a pH electrode.

In another embodiment of the invention, the at least one apparatus can also be at least one port for a rinsing and/or calibration medium inlet and outlet.

Preferably at least one suction valve is disposed in the wall section. By means of said suction valve, gases, liquids and solids contained in the three-dimensional space formed by the container and the wall section can be drawn off, so that an apparatus disposed on the wall section can be pre-cleaned.

In another preferred embodiment of the invention, at least one port for a rinsing and/or calibration medium inlet and outlet can be disposed in the container, thereby enabling the apparatus to be rinsed and if necessary calibrated.

Advantageously at least one suction valve is disposed in the container, thereby enabling rinsing agent residues adhering to the apparatus after it has been rinsed and before it has been returned to the process to be removed e.g. during maintenance of the apparatus.

The at least one port comprises at least one port for drainage, rinsing and/or buffering.

In a preferred embodiment, the container is connected to a drive which moves the container. Said drive preferably incorporates a motor. The drive can be an electric motor or a pneumatic drive with compressed air or manual.

The at least one apparatus is preferably a pH electrode which is connected to a pH measuring instrument/controller.

In a preferred embodiment of the invention, the wall section has a seal matched to the size of the open end of the container, thereby enabling the closed three-dimensional space formed by the container and the wall section to be reliably sealed with respect to the flow duct and its process medium.

In another embodiment of the invention, the container has a seal at its open end.

According to the inventive method for performing maintenance on at least one apparatus disposed on a wall section of the flow duct, a container movably disposed inside the flow duct is placed over the wall section incorporating the apparatus to be maintained so that the container and the wall section together form a closed three-dimensional space, and maintenance is performed in said closed three-dimensional space.

In a preferred embodiment, the method according to the invention also includes rinsing of the at least one apparatus, thereby enabling firmly adhering particles impairing the operation of the measuring electrode to be removed from apparatuses.

The method according to the invention preferably also includes calibration of the apparatus. For example, a pH electrode can be calibrated prior to further use.

The method according to the invention can also include evacuating the closed three-dimensional space formed by disposing the container on the wall section, thereby enabling a process, rinsing and/or calibration medium to be removed from the wall section and the at least one apparatus. Rinsing and/or calibration medium and the like adhering to the wall section and an apparatus can therefore be removed before the apparatus is returned to the process so that no contaminants are introduced into the process. On the other hand, by evacuating the closed three-dimensional space formed by disposing the container on the wall section, process medium can also be removed prior to the apparatus rinsing and/or calibrating steps, i.e. evacuation of the closed three-dimensional space formed by disposing the container on the wall section enables the apparatus to be pre-cleaned.

In a further embodiment, the method includes removing the at least one apparatus and/or installing at least one apparatus. By disposing the container on the wall section of the flow duct on which the apparatus is disposed such that the apparatus is enclosed by the container and the wall section, it becomes possible, for example, to replace a defective apparatus during an ongoing process. In addition, forming the closed three-dimensional space makes it possible to incorporate further measuring instruments into the wall section of the flow duct.

Other possible methods are pH determination in dye syntheses, pH determination in carbonation (sugar processing), pH determination in industrial and municipal sewerage systems.

The method is preferably carried out for performing maintenance on an electrode. The method according to the invention is particularly suitable for a pH electrode used to measure the pH value of a milk of lime suspension of a flue gas scrubber.

BRIEF DESCRIPTION OF THE DRAWINGS

Further features, characteristics and advantages of the present invention will now be described on the basis of exemplary embodiments and with reference to the accompanying drawings in which.

DETAILED DESCRIPTION OF INVENTION

Figure 1:
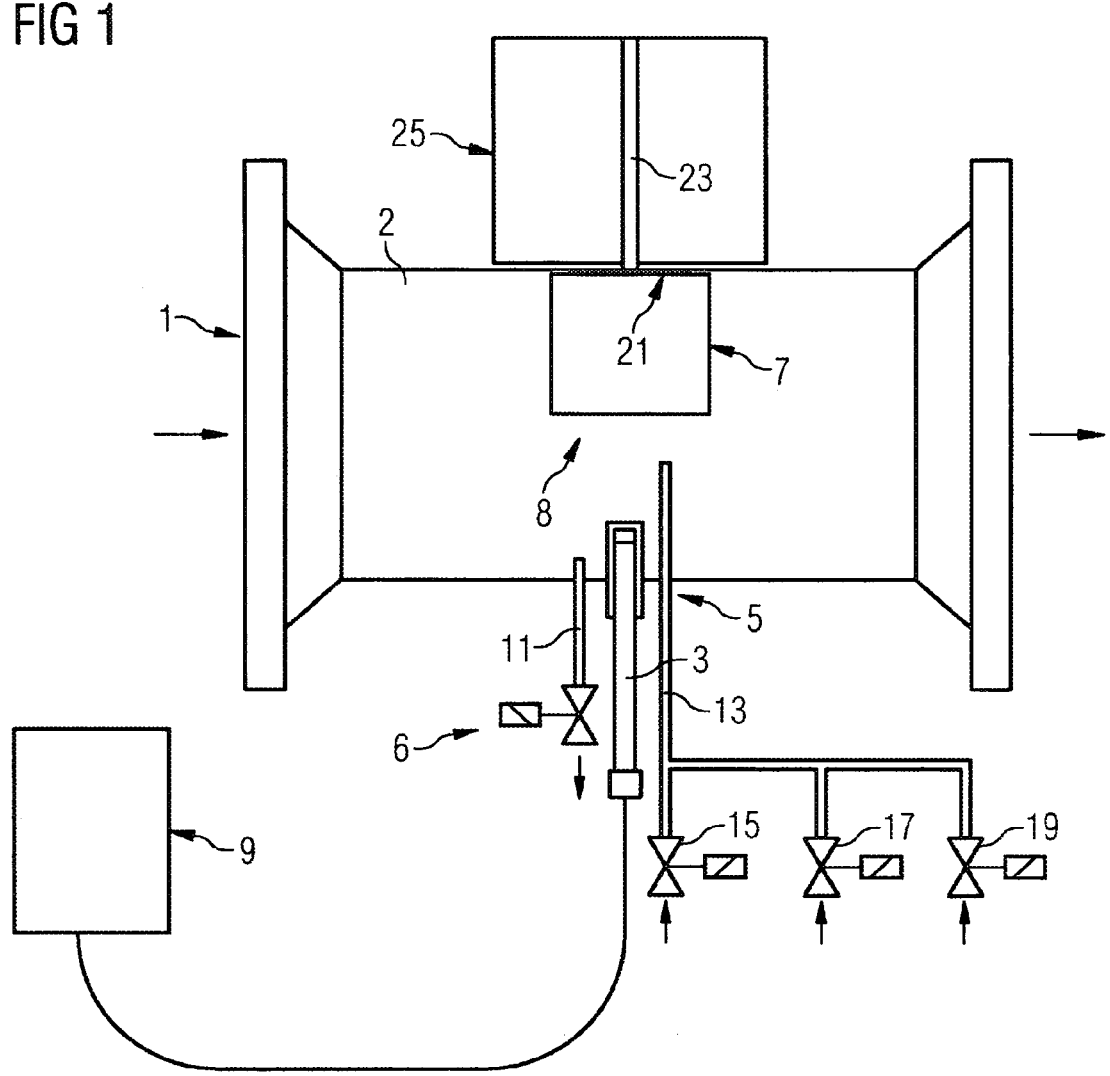
FIG. 1 shows an embodiment of the device according to the invention wherein an apparatus is in the operating position.
Figure 2:
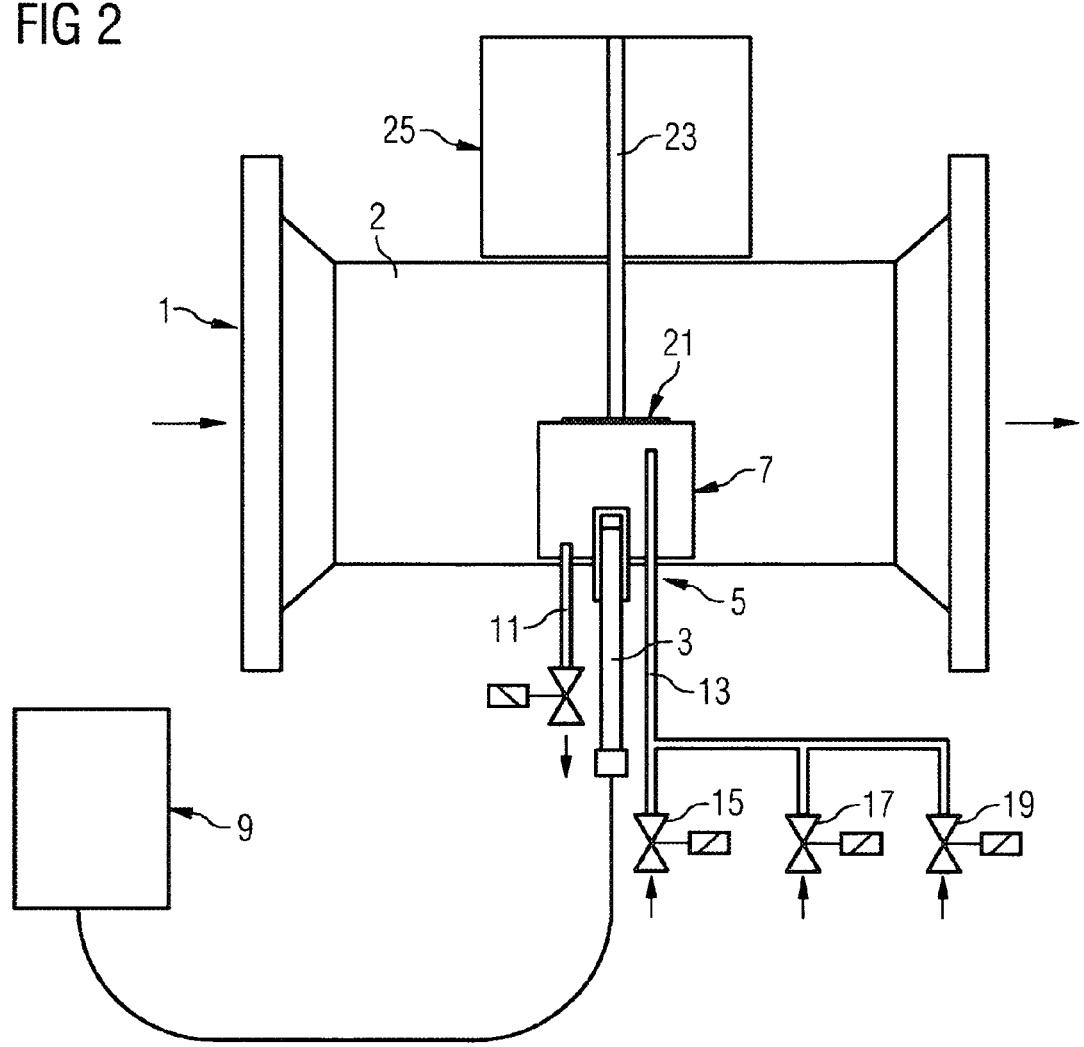
FIG. 2 shows an embodiment of the device according to the invention wherein an apparatus is in the maintenance position.

FIGS. 1 and 2 show a section of a flue gas scrubber as an example of the device according to the invention. The latter comprises a flow duct 1 which is formed by a pipe section 2 of the flue gas scrubber and in which a movable sleeve 7 is disposed. The latter comprises a tube having an open end 8 and an end closed with a plate 21.

The sleeve 7 is movably disposed inside the pipe section in a direction perpendicular to the axial direction of the pipe section 2 and can be displaced from an operating position (FIG. 1) into a maintenance position (FIG. 2). In the maintenance position, the open end 8 of the sleeve 7 lies against a wall section 5 of the pipe section 2, the wall section 5 and the sleeve 7 forming a closed three-dimensional space. The closed three-dimensional space is sealed against the medium flowing in the pipe section 2 by means of a seal disposed between the wall section 5 and the sleeve 7.

On the wall section 5 there is disposed an apparatus 6 which in the present example comprises a pH measuring electrode 3, a drainage port 11 and a feed port 13 with a number of valves 15, 17, 19. When the sleeve 7 is in the end position shown in FIG. 2, the measuring electrode 3, the drainage port 11 and the feed port 13 are within the closed and sealed three-dimensional space.

The pH electrode 3 is connected to a pH measuring instrument/controller 9 and is used to measure the pH value of the medium in the pipe section 2. A rinsing medium and two different buffer solutions for rinsing and calibrating the electrode can be fed through the port 13 using the valves 15, 17 and 19.

The sleeve 7 is connected to a rod 23 by means of the plate 21. This arrangement is part of a drive 25 comprising a motor (not shown) for moving the rod 23 and thereby the sleeve 7 from one end position to the other. The drive 25 can be an electric motor or a pneumatic drive with compressed air or manual.

In the embodiment shown in FIG. 1, the electrode 3 is in the operating position, i.e. the electrode 3 is measuring the pH value of the medium flowing through the flow duct 1.

FIG. 2 shows the same embodiment of the device according to the invention as in FIG. 1 but with the electrode 3 in the maintenance position, i.e. the movable sleeve 7 is on the wall section 5 on which the electrode 3 and the ports 11 and 13 are disposed such that they form a closed three-dimensional space with the wall section 5.

By opening the valve 15, the electrode 3 is rinsed via the port 13 and rendered free of contamination. The rinsing medium is removed from the three-dimensional space formed by the sleeve 7 and the wall section 5 by opening the port 11. When rinsing of the electrode 3 is complete, it is ensured that the port 11 and valve 15 are closed. By opening the valve 17, the electrode 3 is then exposed to a buffer solution which can be removed from the three-dimensional space formed by the sleeve 7 and the wall section 5 by opening the port 11. By opening the valve 19, the electrode 3 is exposed to a second buffer solution which can in turn be removed from the three-dimensional space by opening the port 1. After removal of the second buffer solution, calibration of the electrode 3 is complete.

The sleeve 7 is moved by actuating the drive 25 and is disposed at a distance from the wall section 5 so that the sleeve 7 forms no closed three-dimensional space with the wall section 5. The electrode 3 is then once again in the operating position.

In the example described, a drainage port 11 is disposed in the wall section 5 of the pipe section 2. Alternatively, at least one suction opening can be disposed in the sleeve 7, the extracted medium being able to be removed e.g. by the rod 23 if it is made hollow so that it forms a tube. Finally, it is also possible that suction takes place both via the drainage port and via the suction opening.

The invention claimed is:

1. A device, comprising:
 a flow duct having a wall section;
 a pH electrode arranged along the wall section, projecting into the flow duct and requiring maintenance after a particular operating time; and
 a container is arranged in the flow duct and opens toward the pH electrode, wherein the container is movable relative to the wall section such that, in a first position, the container is disposed at a distance from the pH electrode and, in a second position, forms together with the wall section a closed three-dimensional space separate from the rest of the flow duct such that the pH electrode is enclosed in the container.

2. The device as claimed in claim 1,
 wherein the apparatus pH electrode further comprises a port for a rinsing.

3. The device as claimed in claim 2,
 wherein the port for a rinsing is arranged in the container.

4. The device as claimed in claim 3,
 wherein the port comprises a port for drainage, for rinsing and/or for buffering.

5. The device as claimed in claim 2,
 wherein the pH electrode is connected to a pH measuring instrument/controller.

6. The device as claimed in claim 1,
 wherein a suction valve is arranged in the wall section.

7. The device as claimed in claim 1,
 wherein the container is connected to a drive controlling the movement of the container between the first position and the second position.

8. The device as claimed in claim 1,
 wherein the wall section has a seal matched to the size of the open end of the container.

9. The device as claimed in claim 1,
 wherein the container has a seal at its open end.

10. The device as claimed in claim 1,
wherein the apparatus further comprises a port for a rinsing and/or calibration medium inlet and outlet.

11. The device as claimed in claim 1,
wherein a port for a calibration medium inlet is arranged in the container.

12. The device as claimed in claim 11,
wherein the port comprises a port for drainage, for rinsing and/or for buffering.

13. The device as claimed in claim 1,
wherein the container is arranged in a pipe section in a direction perpendicular to an axial direction of the pipe section such that movement of the container between a first position and a second position is perpendicular to the axial direction of the pipe section.

14. The device as claimed in claim 1,
wherein a medium flowing in the flow duct is prevented from entering the container when the container is in the second position.

15. A method for performing maintenance on a pH electrode, comprising:

providing a device, which includes the pH electrode, as claimed in claim 1;

covering the pH electrode with the container such that the container forms together with the wall section a closed three-dimensional space; and performing maintenance on the pH electrode in the closed three-dimensional space.

16. The method as claimed in claim 15,
wherein maintenance comprises rinsing the pH electrode.

17. The method as claimed in claim 15,
wherein maintenance comprises calibration of the pH electrode.

18. The method as claimed in claim 15,
wherein maintenance comprises evacuation of the closed three-dimensional space.

19. The method as claimed in claim 15,
wherein maintenance comprises removal and/or installation of the pH electrode.

* * * * *